United States Patent [19]

Bookstaber

[11] Patent Number: 4,863,382

[45] Date of Patent: Sep. 5, 1989

[54] RETENTION SYSTEM FOR DENTAL PROSTHESIS

[76] Inventor: Stanley A. Bookstaber, 75 Lakeside Dr., Marlton, N.J. 08053

[21] Appl. No.: 220,840

[22] Filed: Jul. 18, 1988

[51] Int. Cl.[4] .............................................. A61C 13/22
[52] U.S. Cl. .................................................... 433/172
[58] Field of Search .............. 433/172, 178, 181, 182, 433/183

[56] References Cited

U.S. PATENT DOCUMENTS

| | | |
|---|---|---|
| 377,970 | 2/1888 | Waters . |
| 688,661 | 12/1901 | Miller . |
| 4,604,060 | 8/1986 | Weissman . |
| 4,627,136 | 12/1986 | Kreylos et al. . |
| 4,681,542 | 7/1987 | Baum . |

FOREIGN PATENT DOCUMENTS 3706816 9/1987 Fed. Rep. of Germany ...... 433/172
496376 9/1954 Italy ..................................... 433/172

*Primary Examiner*—Robert Peshock
*Attorney, Agent, or Firm*—Connolly & Hutz

[57] ABSTRACT

A retention system for dental prosthesis includes an undercasting which is secured to a tooth. A pair of inner shell members are provided, one on each side of the undercasting. A prosthesis is mounted over the undercasting and includes a pair of outer shell members, each of which is disposed against the inner shell member to form a shroud. A resilient pin is seated in the shroud to provide for positive retention of the prosthesis to hold it in place while still permitting its removal.

14 Claims, 1 Drawing Sheet

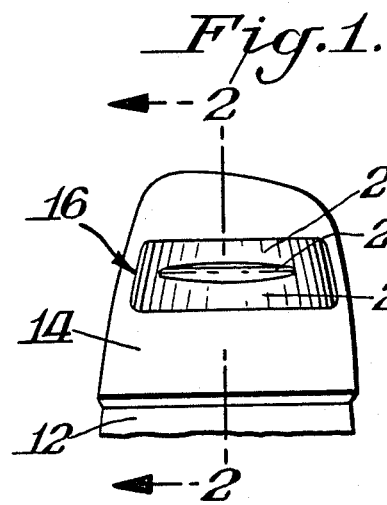
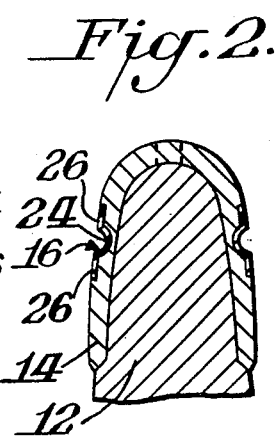
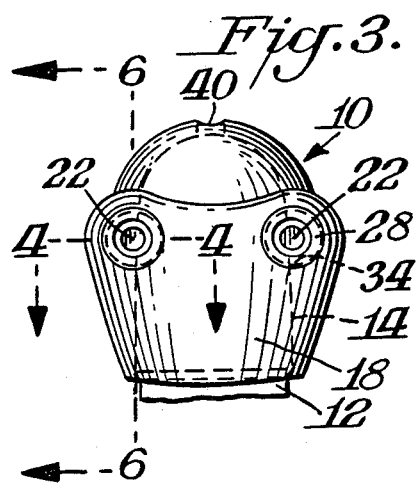
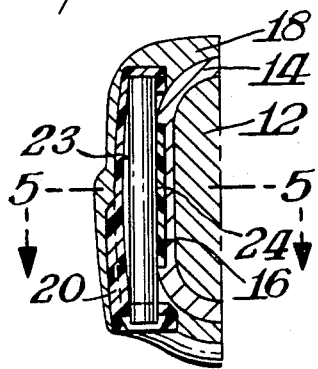
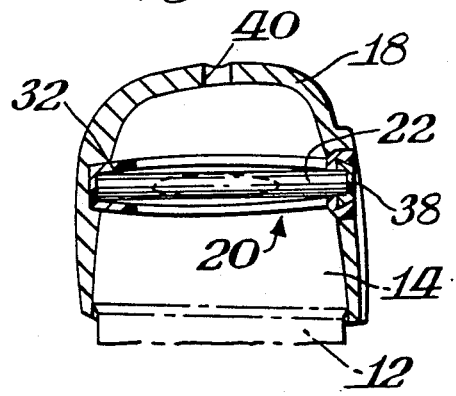
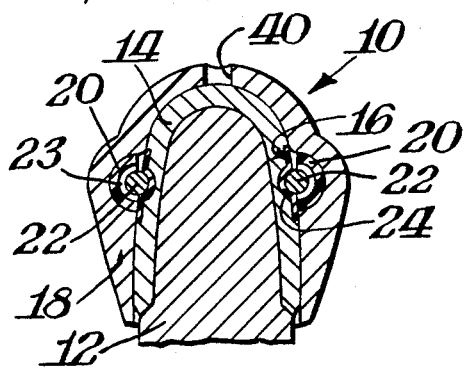
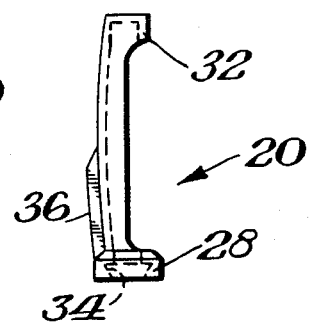
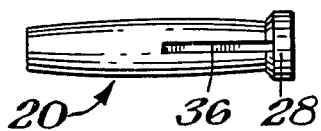
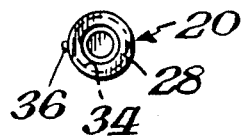
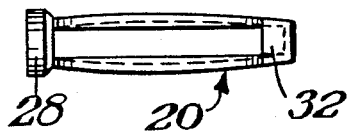

RETENTION SYSTEM FOR DENTAL PROSTHESIS

BACKGROUND OF INVENTION

The present invention relates to a retention system for dental prosthesis such as crowns and bridges. In general, the prior art has used various means to secure the prosthesis in place. Such means, however, have resulted in ineffective or permanent attachment of the prosthesis or in the use of such complicated systems as to render it difficult to remove the prosthesis. It would be desirable if a system could be provided wherein the prosthesis could be easily mounted in place in a secure manner and yet readily removed for repair or replacement or cleansing.

SUMMARY OF INVENTION

An object of this invention is to provide a retention system for dental prosthesis wherein the prosthesis can be readily attached and remain securely in place, while still permitting its removal.

A further object of this invention is to provide such a retention system which could be used for such prosthesis as crown and bridges and partial dentures and implants.

In accordance with this invention, the retention system includes an undercasting which is secured over and to a tooth. A pair of inner shell members is provided with one shell member on each side of the undercasting. The prosthesis itself would be mounted over the undercasting. A pair of outer shell members would be disposed within the prosthesis in juxtaposed relationship to the inner shell members to provide a shroud which is exposed through the prosthesis. A resilient pin or spring would be mounted in each shroud to firmly lock the prosthesis in place and yet permit its ready detachment.

Each shell member may have an arcuate cross section. The inner shell members may have peripheral flanges for proper securement of the inner shell members to the undercasting. Each of the outer shells includes a seat portion for receiving the labial end of the resilient pin with a collar portion exposed at the lingual end of the prosthesis. The collar portion is preferably counter bored so that the pin would terminate in the counter bore area with the area then filled with a suitable resin thereby providing a smooth outer surface and securing the pin in the prosthesis.

THE DRAWINGS

FIG. 1 is a side elevation view of the undercasting and inner shell members of a retention system in accordance with this invention;

FIG. 2 is a cross-seccional view in elevation taken through FIG. 1 along the line 2—2;

FIG. 3 is a rear elevation view showing the retention system of this invention for use with a crown;

FIG. 4 is a cross-sectional view taken through FIG. 3 along the line 4—4;

FIG. 5 is a cross-sectional view taken through FIG. 4 along the line 5—5;

FIG. 6 is a cross-sectional view taken through FIG. 3 along the line 6—6;

FIG. 7 is a front-elevation view of the outer shell member of the outer shell member shown in FIGS. 3-6;

FIGS. 8-9 are side elevation views of the outer shell member shown in FIG. 7; and FIG. 10 is a plan view of the outer shell member shown in FIGS. 7-9.

DETAILED DESCRIPTION

FIG. 5 illustrates the various components of a retention system 10 in accordance with this invention. As shown therein the components include an undercasting 14 which is mounted over and secured to a tooth 12 with a pair of inner shell members 16,16 secured to each side of the undercasting 14. A prosthesis 18 which is illustrated in FIG. 5 as being a crown is detachably mounted to the undercasting. The mounting is effected by means of a pair of outer shell members 20,20 and resilient pins 22,22. Each outer shell member 20 is disposed against an inner shell member 16 to form a shroud into which a respective pin is inserted.

FIGS. 1-2 illustrate the details of the undercasting 14 and inner shell members 16,16. The inner shell members 16,16 are preferably made of a plastic material which may be rigid or resilient and having an arcuate central section 24 with peripheral flanges 26,26. The inner shell members 16 may be made by using the known lost wax technique wherein the members ae seated in an offset stirrup of a mandrel and placed in the wax-up and cast as part of the undercasting 14. The surface of the inner shell members 16 which contact the undercasting 14 are preferably of knurled texture for retention into the wax pattern. The flanges 26,26 are flat and are flush to the wax-up or undercasting. By this procedure the inner shell members 16,16 are in firm contact with the grooves formed in undercasting 14 and thus the inner shell members 16,16 remain securely in place. Undercasting 14 would be mounted to a tooth stub 12 in the manner known in the art.

FIGS. 7-10 illustrate the details of the outer shell members 20. As shown therein, the outer shell members 20 are also made of a suitable plastic material. The proximal end of each outer shell member includes a collar 28 which is exposed at the lingual surface of the prosthesis 18 to provide access to the interior of the shell member 20 and its corresponding inner shell member 16. The distal end of the outer shell member 20 includes a seat portion 32 at the labial or buccal wall for receiving and end of the resilient pin 22. Collar 28 includes a counter bore portion 34 as later described. Each outer shell also includes an anti-twist fin 36. As illustrated in FIG. 10, outer shell 20 is generally curved in its plan view to follow the general contour of the prosthesis. The cross-sectional area of the shroud is slightly larger than the cross-sectional area of the pins 22. A slight space 30 thus results between pin 22 and outer shell 20 over the length between collar 28 and seat 32. Thus, pin 22 is generally anchored against bending movement at collar 28 and seat 32 but permitted to slightly bend or bow outwardly when the prosthesis 18 is to be removed, as later described.

Each outer shell member 20 would be located on the inner surface of the prosthesis 18 in a suitably formed groove by utilizing rods during the forming step of shell members 20 thereby giving shells 20 their proper shape. The fins 36 prevent any twisting or rotation, which might otherwise displace the outer shell members 20.

As shown in FIG. 5, when prosthesis 18 is mounted over undercasting 14, each outer shell member 20 is juxtaposed an inner shell member 16 so as to form a shroud into which the pins 22 are inserted through collar 28 until the pins rest in seat 32. The pins may be pre-cut so as to terminate in the recessed counter bore portion 34 and thus not protrude from the prosthesis. The counter bore portion 34 would next be filled with a dental resin 38 or acrylic or soldering in a manner known in the art. See FIG. 6.

The provision of pins 22 in the shrouds resulting from inner shells 16 and outer shells 20 provide a positive retention of the prosthesis 18 to hold it firmly in place. When, however, it is desired to remove the prosthesis all that is necessary is to apply a force pulling prosthesis 18 outwardly away from undercasting 14. Becaue pins 22,22 are made of springy or resilient material, the pins bow outwardly away from inner shells in the region between collar 28 and seat 32. Since collar 28 and seat 32 are located outwardly beyond inner shells 16,16 such outward bowing removes pins 22,22 from inner shells 16,16 thereby permitting the prosthesis 18 to be detached.

A particularly notable advantage of the present invention is that it permits the use of non-precious metals such as chromium-nickel alloys to be used for the prosthesis, whereas the prior art was limited to noble metals in order to mount such prosthesis in place.

The overall length of the outer shells 20,20 is preferably 10 mm. posterior and 7 mm. anterior with an overall heighth of 2 mm. The overall heigth of the flanges 26,26 of inner shells 16,16 is 4 mm. with a 0.5 mm. undercut on the interior aspect between the flanges. As previously noted shells 20,20 are made with the use of rods, preferably carbon rods or ceramic cores. Carbon rods would be used with precious alloys and ceramic cores could be used for non-precious alloys. The spring wires of pins 22,22 are pre-cut from anterior or posterior size and could be available separately for replacement purposes. Preferably 20 gauge spring wire would be used for pins 22,22. Collar 28 would have a length of 1.5 mm. and seat 32 would likewise have a length of 1.5 mm.

As is apparent from the retention system 10 of this invention is thus a significant advancement over the prior art in that it provides a means for ready attachment of a prosthesis such as a crown or bridge to a tooth, while providing for a secure attachment, yet still permits the ready detachability of the prosthesis for replacement or repair purposes or daily cleansing.

What is claimed is:

1. A retention system for dental prosthesis comprising an undercasting, a pair of inner shell members secured to opposite sides of said undercasting, a prosthesis mounted over said undercasting, a pair of outer shell members mounted to the inner surface of said prosthesis, each of said outer shell members being disposed against a respective one of said inner shell members to form a shroud exposed at the lingual face of said prosthesis, and a resilient pin mounted in each of said shrouds to provide positive retention of said prosthesis.

2. The system of claim 1 wherein each of said outer shell members includes a seat at its buccal or labial end and a collar at its lingual end, each of said pins being seated at one end in said seat and at its other end in said collar.

3. The system of claim 2 wherein said seat and said collar are located beyond said inner shell.

4. The system of claim 3 wherein said shroud is of larger cross-sectional area than the cross-sectional area of said pin in the portion of said shroud including said inner shell to permit said pin to bow outwardly in said portion.

5. The system of claim 4 wherein said collar includes a counter bore, and said pin terminating in said counter bore.

6. The system of claim 5 wherein said counter bore is filled with a resin to shield said pin and provide a smooth continuous surface which blends with the outer surface of said prosthesis.

7. The system of claim 6 wherein said outer shell includes an anti-twist fin.

8. The system of claim 6 wherein a pair of peripheral flanges are provided on said inner shell.

9. The system of claim 6 wherein said outer shell is curved in its plan view.

10. The system of claim 6 wherein a vent hole is provided in said prosthesis.

11. The system of claim 10 wherein said prosthesis is a crown.

12. The system of claim 10 wherein said prosthesis is a bridge.

13. The system of claim 10 wherein said prosthesis is a partial.

14. The system of claim 10 wherein said prosthesis is an implant restoration.

* * * * *